(12) United States Patent  (10) Patent No.: US 6,435,183 B1
Farman  (45) Date of Patent: Aug. 20, 2002

(54) FLOW SENSING DEVICE

(75) Inventor: David A. Farman, Dana Point, CA (US)

(73) Assignee: Brentwood Medical Technology Corp., Versailles, OH (US)

( * ) Notice: Subject to any disclaimer, the term of this patent is extended or adjusted under 35 U.S.C. 154(b) by 0 days.

(21) Appl. No.: 09/159,125

(22) Filed: Sep. 23, 1998

(51) Int. Cl.$^7$ ............................................. A61M 16/00
(52) U.S. Cl. ................... 128/204.25; 600/529; 600/538
(58) Field of Search ...................... 128/200.24, 204.24, 128/204.25, 205.23, 204.23; 600/366, 484, 529, 532, 533, 537, 538

(56) References Cited

U.S. PATENT DOCUMENTS

| | | | |
|---|---|---|---|
| 3,705,534 A | * 12/1972 | Turek | 73/189 |
| 4,098,290 A | * 7/1978 | Glenn | 128/204.25 |
| 4,573,462 A | * 3/1986 | Baum | 128/204.25 |
| 4,838,257 A | 6/1989 | Hatch | |
| 4,884,460 A | 12/1989 | Nowacki et al. | |
| 4,905,709 A | 3/1990 | Bieganski et al. | |
| 5,038,773 A | 8/1991 | Norlien et al. | |
| 5,040,529 A | 8/1991 | Zalkin | |
| 5,303,698 A | 4/1994 | Tobia et al. | |
| 5,564,432 A | 10/1996 | Thomson | |
| 5,676,132 A | * 10/1997 | Tillotson et al. | 128/204.25 |
| 6,267,006 B1 | * 7/2001 | Bugli et al. | 73/118.2 |

* cited by examiner

Primary Examiner—Glenn K. Dawson
(74) Attorney, Agent, or Firm—Wood, Herron & Evans

(57) ABSTRACT

A fluid sensing device includes a venturi tube and a fluid resistive element. The venturi tube defines a first open end through which a flow of fluid enters, a second open end from which fluid flow exits and a constricted midportion therebetween. The fluid resistive element is located within the venturi tube. In combination with the tube, the fluid resistive element measures flow for accurate sensing of the flow over a range of fluid flow into the tube. A labeled fluid sensing device, includes a fluid flow sensing tube and a label. The label has a first panel secured to a surface of the tube and a second optically sensable panel removably connected to the first panel.

8 Claims, 4 Drawing Sheets

FLOW SENSING DEVICE

FIELD OF THE INVENTION

The invention is directed to a flow sensing device and a method for sensing flow.

BACKGROUND OF THE INVENTION

Flow sensing devices use physical principles to produce an analog output to measure flow rates. The analog output can also be integrated to calculate flow volumes. Flow sensing devices include a pressure differential type, which has an air-resistive element that creates a pressure drop, which is proportional to the flow of fluid or air through the tube in which the resistive element is located. A pressure transducer converts the pressure reading into electrical signals, which can be used to determine the air flow rate, which can be integrated to provide volume measurements.

Flow sensing devices can be used for measuring air flow in a respiratory air flow apparatus. Such apparatus can include apparatus for artificial ventilation of a patient, pneumotachometers, equipment for assessing cardiopulmonary performance and evaluating pulmonary function during exercise and static testing, air breathing apparatus such as emergency apparatus and scuba respirators and the like.

The present invention is directed to a pneumotachometer which is a device that measures instantaneous respiratory air flow. In a differential pressure flow transducer pneumotachometer, a sensitive manometer detects a pressure drop across a light resistance placed in the air flow. For example, a Fleisch pneumotachometer utilizes capillary air flow resulting from air flowing through a resistant element made of a bundle of parallel capillary tubes to maintain a linear relationship between flow and pressure difference. The tubes can be layers of bundles of fine metal screen capillaries that cause a linear resistance to lateral flow of air through the tube.

One type of conventional respiratory air sensing device 10 is shown in FIG. 1 from Tillotson et al., U.S. Pat. No. 5,676,132. The device 10 utilizes a venturi-type tube 12. A venturi is a constriction section of a pipe that causes a drop in pressure as fluid flows through the pipe. The venturi 12 includes a short straight or through pipe section 14 between two tapered sections 16, 18 and can be used to measure fluid flow rate through the pipe. The Tillotson et al. device includes a midsection area 14 of lesser diameter that offers a resistance to flow through the tube. In a respiratory device, the constricted midsection area 14 causes the flow of air that is expired 20 or inspired 22 by a subject, user or patient at a first end 24 of the venturi tube 12 to become a laminar stable air flow in the midsection area 14. A sensor 26 such as a microsensor, is arranged in the midsection area 14 with pins 28 extending outside of the venturi tube 12. The sensor 26 protrudes from an inner surface of the tube 12 into the laminar air flow to detect the flow rate of air therethrough. The sensor 26 then sends detections signals to a microprocessor (not shown) via the pins 28 and a connector 30.

Flow through the venturi tube can be represented by a Bernoulli model where as the cross section of the tube is restricted, flow velocity increases. So long as flow through a tube is laminar (non turbulent), change in pressure created by restricting walls of the tube is described by the equation $\Delta P = a\eta V + b\gamma V^2$ where V is gas flow, $\eta$ is dynamic viscosity, $\gamma$ is gas density and a and b are constants determined by the flow tube characteristics and type of restriction. In the case of the venturi, and assuming an isothermic system and an incompressible fluid, pressure drop created by the cross sectional area of the restriction is represented by $\Delta P = C\gamma V^2$ and change in pressure in the tube is represented by $\Delta P = a\eta V + b\gamma V^2 - C\gamma V^2$. The relationship can be reduced to a simple linear relationship, $\Delta P = a\eta V$.

A problem with venturi-type air sensing devices is the inability to accurately sense flow across a full range of flow rates. For example, at low flow rates, the Reynolds number of the fluid exceeds a critical level and the fluid flow becomes turbulent and non uniform. In turbulent flow, local velocities and pressures of fluid fluctuate irregularly and in a random manner. This results in a non-linear relationship between fluid flow and pressure. Further at low flow rates, the converging shape of the venturi section may reflect back flow to give incorrect readings.

The present invention is directed to a combined pressure change sensing mechanism that provides accurate measurement of pressure difference of turbulent flow as well as of linear flow. In another aspect, the present invention is directed to a disposable fluid sensing device that is easy to manufacture and that includes a safety feature to prevent multiple use.

SUMMARY OF THE INVENTION

The fluid sensing device of the invention comprises a venturi tube and a fluid resistive element. The venturi tube defines a first open end through which a flow of fluid enters, a second open end from which fluid flow exits and a constricted midportion therebetween. The fluid resistive element is located within the venturi tube. In combination with the tube, the fluid resistive element measures flow for accurate sensing of the flow over a range of fluid flow into the tube.

In another aspect, the invention relates to a labeled fluid sensing device, comprising a fluid flow sensing tube and a label. The label comprises a first panel secured to a surface of the tube and a second optically sensable panel removably connected to the first panel.

In another aspect, the invention relates to a process of evaluating fluid flow. In the process a venturi tube and a fluid resistive element located within the tube are provided. The combination of the resistive element with the venturi tube linearizes flow for accurate sensing of said flow over a range of fluid flow into the tube. Fluid is caused to flow into the venturi tube through the first end to exit the second. The flowing fluid within the tube is sensed to provide flow data according to the fluid flow.

In still another aspect, the invention relates to a respiratory fluid flow monitoring process, wherein a venturi tube, a flow sensor and a flow resistive element are provided. The venturi tube includes a first open end through which a flow of fluid enters, a second open end from which fluid flow exits and a constricted midportion therebetween. The flow sensor is positioned within the tube midportion to provide flow data on the fluid flowing through the venturi tube. The fluid resistive element is located within the venturi tube at a location between the first open end and the flow sensor to linearize flow of fluid across a range of flow rates. Fluid is caused to flow into the venturi through the first end to exit the second end. The flowing fluid is sensed with the flow sensor to provide flow data and a flow of the fluid is adjusted according to the flow data.

In a final aspect of the invention, a fluid flow process comprises inserting a tube into a fluid flow system, monitoring the insertion of the tube with an optical sensor to determine absence or presence of an optically sensed indicia on the tube and terminating the process if the monitoring determines that the optically sensed indicia is absent.

BRIEF DESCRIPTION OF THE DRAWINGS

The invention is more readily understood and appreciated by reference to the following Drawings.

DESCRIPTION OF A PREFERRED EMBODIMENT

Figure 1:
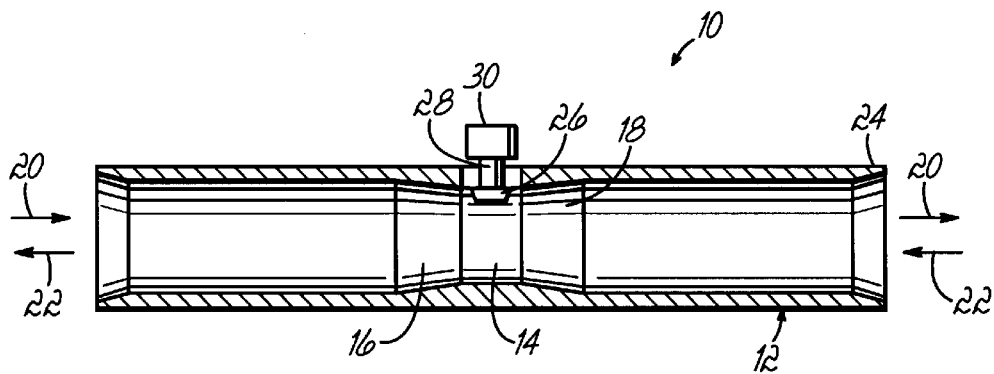
FIG. 1 is a prior art respiratory air sensing device.
Figure 2:
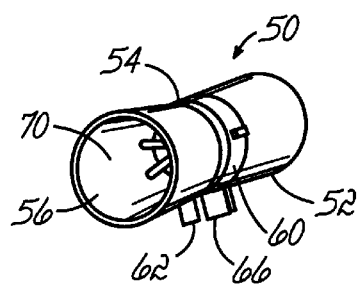
FIG. 2 is a perspective view of an air sensing device according to the invention.
Figure 4:
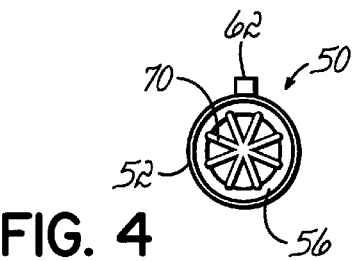
FIG. 4 is a front elevation view of the air sensing device.
Figure 3:
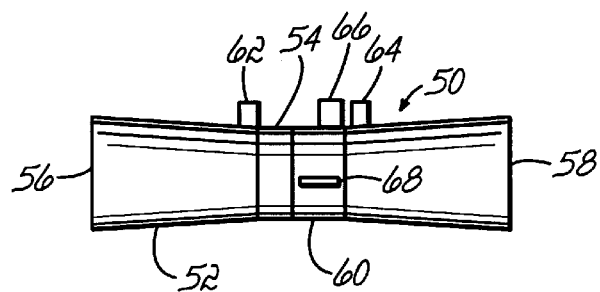
FIG. 3 is a side elevation view of the air sensing device.

FIGS. 2 to 4 show preferred embodiments of the fluid sensing device of the present invention. In the Figures, the fluid sensing device is a spirometer flow-through tube 50 used in connection with a patient respirator as hereinafter described. The tube 50 has a substantially tapered barrel shaped body 52 having a constricted midportion 54 that forms a venturi. The body 52 includes a first open end 56 through which a flow of fluid enters, a second open end 58 from which fluid flow exits and the constricted venturi midportion 54 therebetween. The body 52 includes an indented plane 60 that accommodates a reflective marking label as hereinafter described with respect to FIGS. 8 to 11. The body 52 has two pressure tap ports 62, 64 and a combination extrusion 66 and slot keying mount 68 for mounting to a bracket of a respiratory device. The body 52 as shown, is a single integral injection molded plastic part.

Figure 5:
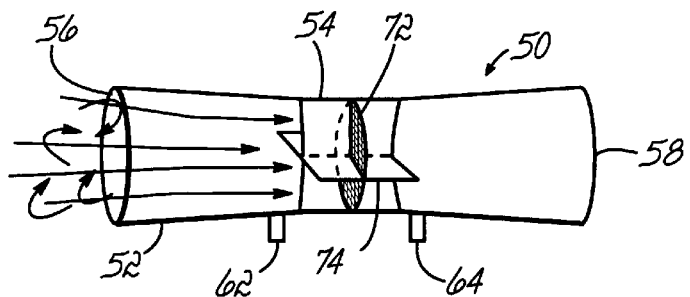
FIG. 5 is a schematic representation of another embodiment of the invention.
Figure 6:
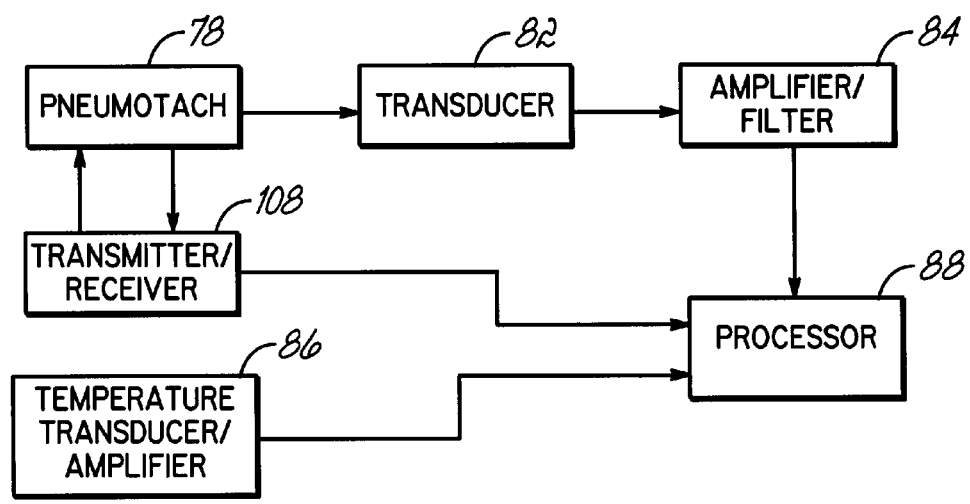
FIG. 6 is a plot of pressure against flow to compare an air sensing device according to the invention with other air sensing devices.

The body 52 also includes a fluid resistive element, which is shown as a plurality of radially extending foils 70 in FIGS. 2 and 4 and as a combination screen 72 and cruciform foil 74 in FIG. 5. The screen 72 can be a wire or cloth network positioned transverse to flow of fluid through the body 52. The combined flow resistive element and venturi transfer functions are additive and result in a usable pressure signal over an entire physiological range. The combined effect of both functions is illustrated in FIG. 6 showing a plot of resultant combined flow versus pressure. As illustrated, the combination of the resistive element and venturi provides accurate and linear pressure measurement across a range of flow rates and even at low flow rates. Any nonlinearity of the combined curve is easily compensated for by correction via a microprocessor as described next with reference to FIG. 7.

Figure 7:
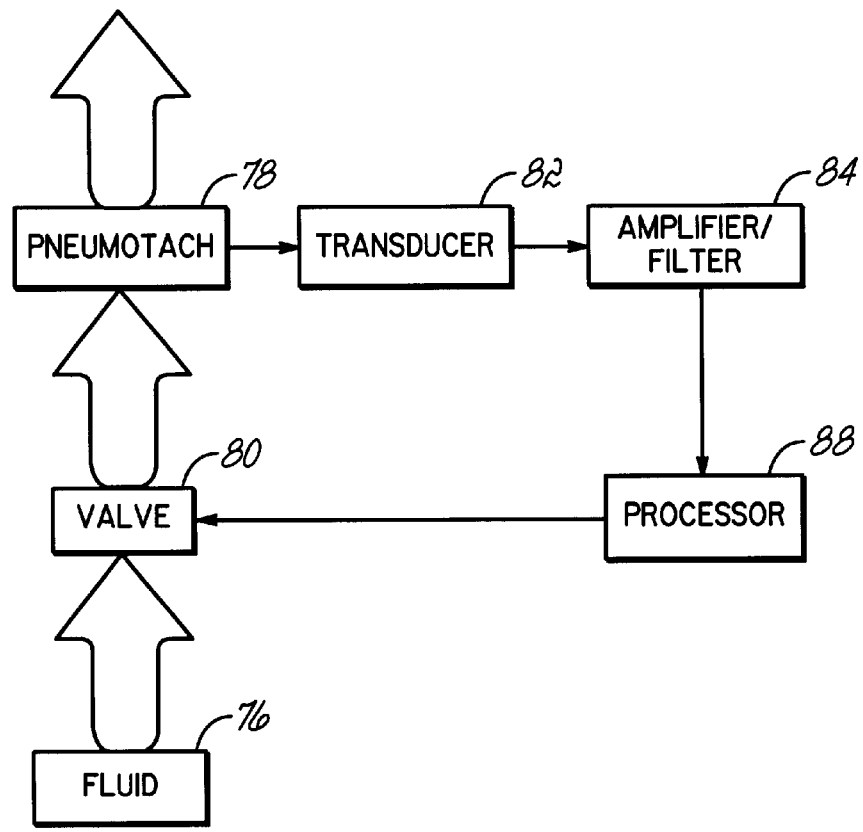
FIG. 7 is a schematic representation of a method of evaluating fluid flow according to the invention.

FIG. 7 shows a lung function testing system that includes an inspiration/expiration pneumotachometer 78, which can be included in a mouthpiece connectable to a patient. Differential pressure sensed by the pneumotachometer is pneumatically coupled to a precision differential pressure transducer 82 that is selected for its low noise and drift, as well as immunity to change in temperature. The transducer 82 converts the pressure difference sensed by the pneumotachometer 78 to an electrical signal. The signal from the transducer 82 is processed by an amplifier/filter 84, which can be a series of amplifiers and filters 84 to provide measurement data to processor 88. For example, a series of amplifiers and filters 84 can include an instrumentation amplifier, a low pass filter, a final state gain amplifier and an offset buffer amplifier. The processor 88 can include a controller and a universal asynchonous receiver transmitter. The instrumentation amplifier provides high gain and stability and critical rejection of common mode noise. Most physiological signal information is present in the DC to 18 Hz range. Hence it is important that the transducer be characterized by low frequency response performance and accuracy to encompass at least this range. A $5^{th}$ order switched capacitor filter can provide sharp high frequency upper band high frequency rejection and a Butterworth type active filter circuit can further reduce clock frequency noise. A final offset and gain stage amplifier can produce a signal for input to an A/D converter that exhibits low noise, low drift, high stability and accuracy characteristics.

Processor 88 receives the amplified and filtered signal and provides flow data for evaluation of a subject's lung function. The processor 88 can be a series of converters and/or microprocessors including a micro-controller, a universal asynchronous receiver transmitter and a computer. Processor 88 can be an embedded computer, a separate PC or a combination thereof. The universal asynchronous transmitter receiver, part of processor 88, can be used in full duplex mode to allow transmission and reception of commands to an external computer or PC. The processor 88 performs calculations of flow linearization, flow rate and air volume, as required by the application. Transmitter/receiver 108 can be a light emitting diode and detector and preferably is an infrared transmitter/receiver. The function of the transmitter/receiver 108 is described in detail hereinafter. In one embodiment, transducer 82, amplifier/filter 84, transmitter/receiver 108, temperature transducer/amplifier 86 and processor 88 are integrated into a compact handle assembly that can be interfaced to a standard IBM compatible computer for processing of lung function calculations with user interface and report generation. A preferred application of the system of FIG. 7 is the presentation of calculations and graphics for the diagnosis of a patent's lung function.

Ambient temperature can be sensed by temperature transducer/amplifier 86 and processed at the processor 88 to automatically provide a signal calibration correction. Ambient temperature compensation is an important feature of the present invention. Most lung function measurement systems rely on operator calibration prior to testing. Prior calibration is reliable only so long as ambient temperature remains stable. Ambient temperature compensation as provided by the present invention, overcomes problems caused by temperature fluctuation during operation.

Figure 8:
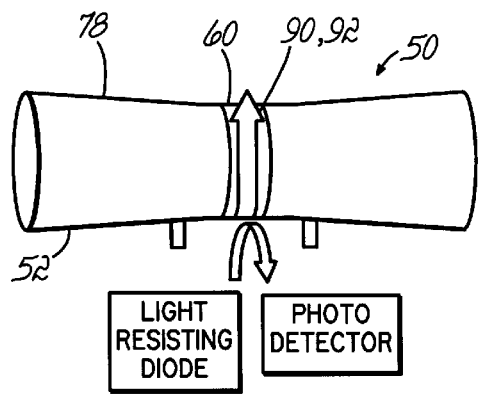
FIG. 8 is a schematic representation of a respiratory fluid flow monitoring process according to the invention.

FIG. 8 shows a respiratory gas flow system that includes a source of pressurized fluid 76 such as oxygen, an inspiration/expiration pneumotachometer 78, which can be included in a mouthpiece connectable to a patient. A controllable demand valve 80 is connected between the gas source 76 and to the pneumotachometer 78. The demand valve 80 controls a flow rate of gas from the gas source 76 to the patient via the pneumotachometer 78 and includes a reference chamber communicating to the gas source 76 to control the valve 80 to send gas to the patient at a positive end of expiration pressure. The pneumotachometer is pneumatically coupled to a transducer 82. The signal from the transducer 82 is processed by an amplifier/filter 84. Processor 88 receives the amplified and filtered signal for processing for control of valve 80. In other embodiments, the tube is a pneumotachometer and flowing fluid is sensed with at least two flow sensors and an output of said sensors is translated into a single signal corresponding to gas flow rate through the fluid sensing device. Flow of the fluid is adjusted according to the signal. An analog voltage is produced proportional to a square root of the output of the sensed flow of fluid. An algebraic sign is affixed to the analog voltage proportional to a square root of the output of the circuit, the signal is compared to a predetermined flow rate and flow of said fluid is adjusted according to the comparing step.

Figure 9:
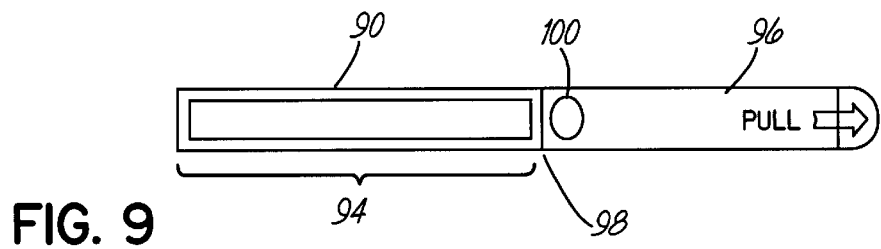
FIG. 9 is a schematic representation of a labeled fluid sensing device according to the invention.
Figure 10:
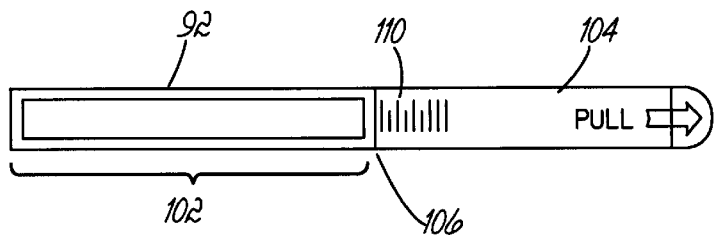
FIG. 10 is a view of a label.
Figure 11:
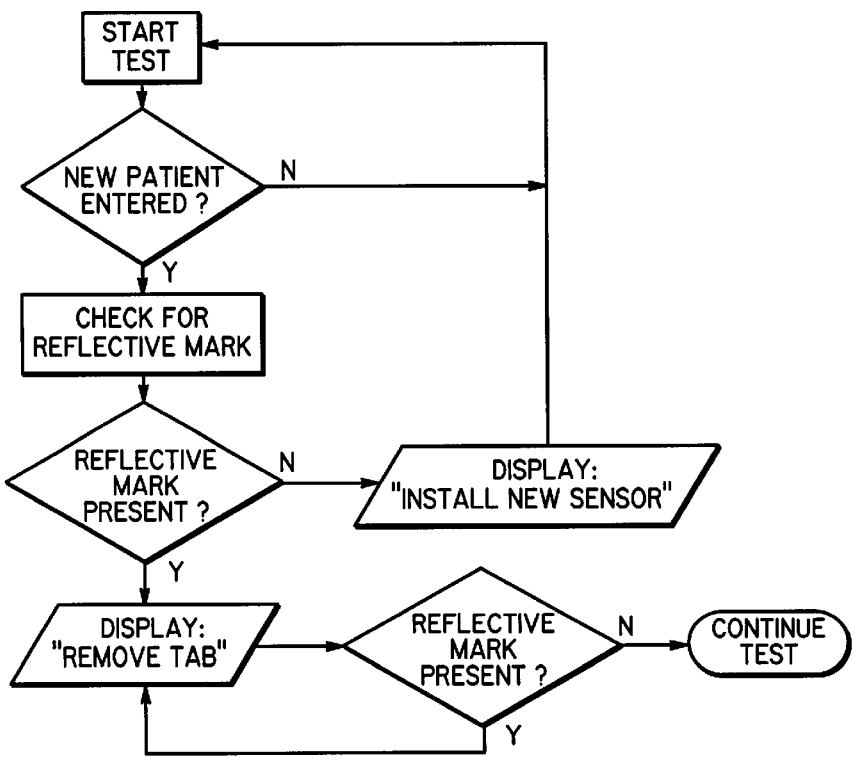
FIG. 11 is a view of another label according to the invention.

In preferred embodiments as shown in FIG. 9, the pneumotachometer 78 is disposable and includes a removable optically sensed label 90 or 92, as shown in FIGS. 10 and 11, to insure single patient use and to eliminate cross contamination and transmission of infections, virus and colds. Labels 90 and 92 permit detection of a newly installed pneumotachometer and determination whether the pneumotachometer was used on a previous patient as illustrated schematically in FIG. 12. The labels 90, 92 are removably attached to the circumference of a disposable pneumotachometer tube 50. The labels 90, 92 include a reflective mark, which is pre-printed on a removable section of the label. FIG. 10 shows a label 90 with two panels. Panel 94 has an adhesive backing to facilitate attachment of the label to a sensing device, for example round the plane 60 of barrel shaped body 52 of tube 50. A second panel 96 is removably connected as a pull tab to the first panel at perforation 98. Panel 96 includes a optically sensitive reflective mark 100. FIG. 11 shows a label 92 again with two panels 102, 104. Panel 102 also has an adhesive backing to facilitate attachment of the label to a sensing device. The second optically sensable panel 104 is removably connected as a pull tab to the first panel at perforation 106. Panel 104 includes an optically readable bar code 110.

Figure 12:
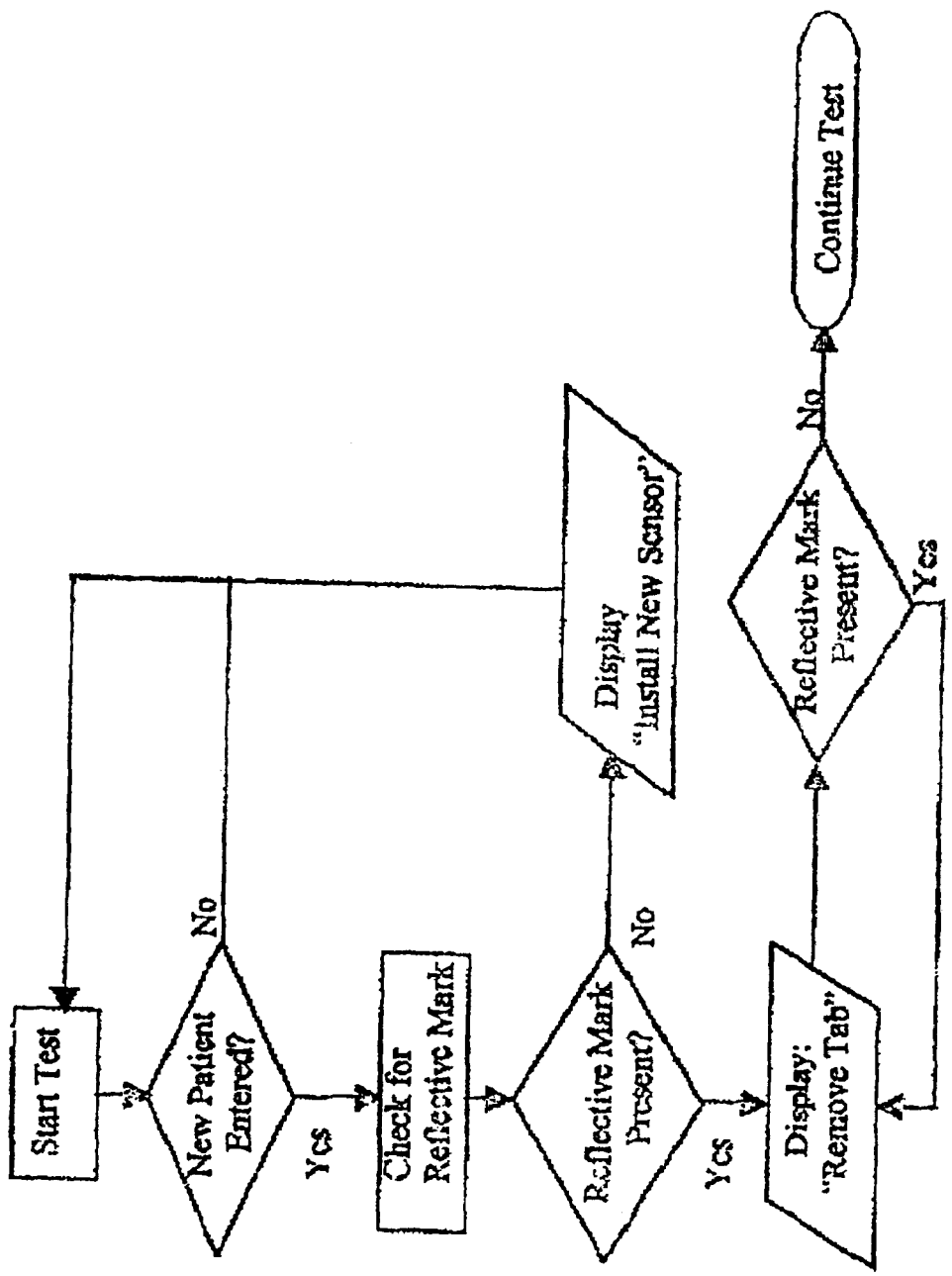
FIG. 12 is a schematic representation of a fluid flow process of the invention.

As shown schematically in FIG. 7, FIG. 9 and FIG. 12, detection is performed optically by the use of an infrared transmitter/receiver 108 mounted in the electronic circuit housing used in combination with the pneumotachometer 78 to detect flow. The transmitter/receiver can be a light emitting diode and photodetector as shown in FIG. 9. When the pneumotachometer 78 is attached to a housing mating interface, the label 90,92 is positioned in close proximity to the infrared transmitter/receiver 108. The disposable pneumotachometer 78 is installed into a respiratory device with use with each new patient. The infrared transmitter/receiver 108 and accompanying circuit senses the presence of the removable label 90,92. A signal from the transmitter/receiver 108 is sent to the processor 88. If label 90, 92 is present, indicating an unused pneumotachometer 78, the processor 88 circuit permits removal of the label 90, 92 and permits further operation of the pneumotachometer 78. If the label 90, 92 is not present, the processor 88 prevents further operation.

Other modifications of the present invention will occur to those skilled in the art subsequent to a review of the present application. These modifications and equivalents thereof are intended to be included within the scope of this invention.

What is claimed is:

1. A fluid flow sensing device comprising:
   a venturi tube defining a first open end through which fluid flow enters, a second open end from which fluid flow exits and a constricted midportion therebetween; and
   a fluid resistive element located within said tube, which in combination with said venturi tube, linearizes flow for accurate sensing of said flow over a range of fluid flow into said tube;
   said fluid resistive element comprising a combination of a cruciform air foil and a wire or cloth network in the form of a screen transverse to flow of fluid through said venturi tube.

2. A fluid flow sensing device comprising:
   a venturi tube defining a first open end through which fluid flow enters, a second open end from which fluid flow exits and a constricted midportion therebetween;
   a fluid resistive element located within said tube, which in combination with said venturi tube, linearizes flow for accurate sensing of said flow over a range of fluid flow into said tube;
   said tube including flow sensing taps positioned adjacent to the tube midportion to sense a pressure differential between said taps across said midportion; and
   a pressure transducer coupled with said flow sensing taps for translating a pressure differential output from said taps into an electrical signal corresponding to gas flow rate differential through said fluid sensing device.

3. The fluid sensing device of claim 2, further comprising a temperature sensor operatively coupled to said device to measure ambient temperature and to adjust said electrical signal corresponding to gas flow rate through said fluid sensing device according to change in ambient temperature.

4. A lung function testing system, comprising the fluid flow sensing device of claim 2 and a microprocessor to process said electrical signal to evaluate lung function according to a fluid flow rate through said device.

5. A respiratory gas flow system, comprising:
   (A) the fluid flow sensing device of claim 2;
   (B) an inspirary flow controller for control of fluid flow into said first open end of said venturi tube; and
   (C) a microprocessor controllably coupled to said inspirary flow controller and coupled to said transducer to compare a signal from said transducer indicative of a pressure with a signal for a desired pressure and to exercise an inspirary control function through said inspirary flow controller to cause said controller to adjust flow to result in a pressure of fluid into said venturi tube to substantially equal said desired pressure.

6. A process of evaluating respiratory fluid flow comprising:
   (A) providing a venturi tube defining a first open end through which fluid flow enters, a second open end from which fluid flow exits and a constricted midportion therebetween; and a fluid resistive element located within said tube, which in combination with said venturi tube, linearizes flow for accurate sensing of said flow over a range of fluid flow into said tube;
   (B) flowing fluid into said venturi tube through said first end to exit said second end;
   (C) sensing said flowing fluid within said tube to provide flow data according to said fluid flow; and
   (D) evaluating lung function according to said flow data.

7. A process of evaluating respiratory fluid flow comprising:
   (A) providing a venturi tube defining a first open end through which fluid flow enters, a second open end from which fluid flow exits and a constricted midportion therebetween; and a fluid resistive element located within said tube, which in combination with said venturi tube, linearizes flow for accurate sensing of said flow over a range of fluid flow into said tube;

(B) said fluid resistive element comprising a combination of a cruciform air foil and a wire or cloth network in the form of a screen transverse to flow of fluid through said venturi tube;
(C) flowing fluid into said venturi tube through said first end to exit said second end;
(D) sensing said flowing fluid within said tube to provide flow data according to said fluid flow.

8. A respiratory fluid flow monitoring process comprising:
(A) providing a venturi tube including a first open end through which a flow of fluid enters, a second open end from which fluid flow exits and a constricted midportion therebetween; a flow sensor positioned within said tube midportion to provide flow data on the fluid flowing through said venturi tube; and a fluid resistive element comprising a combination of a cruciform air foil and a wire or cloth network in the form of a screen transverse to flow of fluid through said venturi tube located within said venturi tube at a location between said first open end and said flow sensor to linearize flow of said fluid at low flow rates;
(B) flowing fluid into said venturi tube through said first end to exit said second end;
(C) sensing said flowing fluid with said flow sensor to provide said flow data; and
(D) adjusting a flow of said fluid according to said flow data.

* * * * *

UNITED STATES PATENT AND TRADEMARK OFFICE
CERTIFICATE OF CORRECTION

PATENT NO.   : 6,435,183 B1
DATED        : August 20, 2002
INVENTOR(S)  : David A. Farman It is certified that error appears in the above-identified patent and that said Letters Patent is hereby corrected as shown below:

Column 1,
Line 61, "(non turbulent)" should be -- non-turbulent --.
Line 67, "cross sectional area" should be -- cross-sectional area --.

Column2,
Line 9, "and non uniform." should be -- and non-uniform. --.

Column 3,
Line 55, "illustrated in FIG. 6 showing a ..." should be -- illustrated in FIG. 4 showing a ... --.

Column 4,
Line 45, "patent's lung function." should be -- patient's lung function. --.

Signed and Sealed this

Eighth Day of April, 2003

JAMES E. ROGAN
*Director of the United States Patent and Trademark Office*